United States Patent [19]

Li et al.

[11] Patent Number: 5,686,631
[45] Date of Patent: Nov. 11, 1997

[54] ASYMMETRIC SYNTHESIS OF R AND S WARFARIN AND ITS ANALOGS

[75] Inventors: Hui-Yin Li; Andrea Jane Robinson, both of Newark, Del.

[73] Assignee: The DuPont Merck Pharmaceutical Company, Wilmington, Del.

[21] Appl. No.: 678,211

[22] Filed: Jul. 11, 1996

Related U.S. Application Data

[60] Provisional application No. 60/001,127 July 13, 1995.
[51] Int. Cl.[6] .................................................. C07D 311/02
[52] U.S. Cl. ............................................................ 549/285
[58] Field of Search ............................................. 549/285

[56] References Cited

U.S. PATENT DOCUMENTS 5,171,892  12/1992  Burk .......................................... 568/12

OTHER PUBLICATIONS

Fasco et al, *J. Medicinal Chemistry* 21(10), 1054–59 (1978).
Ohta et al., *J. Org. Chem.* 60, 357–363 (1995).
Cook et al., *J. Pharmacol. Exp. Ther.* 210(3), 391–398 (1979).
Armstrong et al., *Anal. Chem.* 66, 4278–4282 (1994).
Soini et al., *Anal. Chem.* 66, 3477–3484 (1994).
Bargmann–Leyder et al., *Chromatographia* 37(7/8), 433–443 (1993).

*Primary Examiner*—Amelia Owens
*Attorney, Agent, or Firm*—David H. Vance

[57] ABSTRACT

The present invention provides a novel process for making compounds of formula 2a or 2b or pharmaceutically acceptable salts thereof,

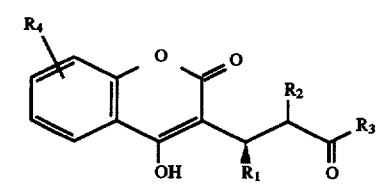
(2a)

-continued
or

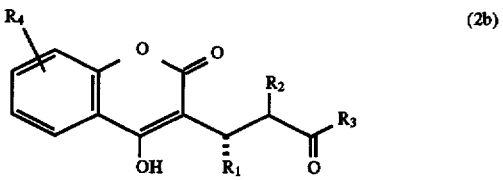
(2b)

wherein R1 is selected from the group consisting of phenyl and phenyl substituted with at least one group selected from $NO_2$ and halogen;

$R_2$ is H;

$R_3$ is selected from the group consisting of $C_{1-4}$ alkyl, phenyl, and benzyl; and, $R_4$ is selected from the group consisting of H and halogen;

which comprises the steps of:

a) oxidizing a racemate of formula 2 or a salt thereof to form a dehydro-compound of formula 3,

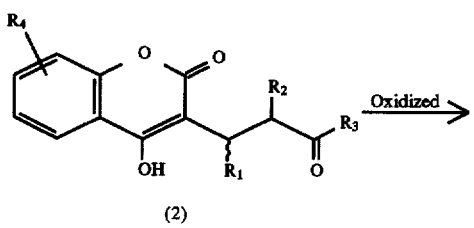
(2)

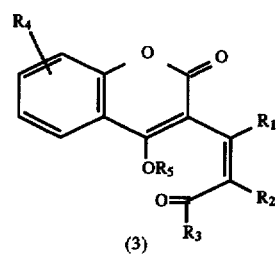

(3)

wherein $R_5$ is selected from the group consisting of H, $CH_3$, benzyl, $C_{2-8}$ acyl Na, Li and K; and, b) asymmetrically hydrogenating a compound of formula 3 in the presence of a chiral phosphine catalyst to form a compound of formula 2a or 2b.

20 Claims, No Drawings

ASYMMETRIC SYNTHESIS OF R AND S WARFARIN AND ITS ANALOGS

This application claims benefit of U.S. Provisional Application No. 60/001,127, filed Jul. 13, 1995.

FIELD OF THE INVENTION

The present invention relates generally to processes for the preparation of R and S warfarin and its analogs from their corresponding racemates.

BACKGROUND OF THE INVENTION

Coumadin®, the most widely prescribed anti-thrombotic in North America, results in decreased activity of clotting factors II, VII, IV and X by inhibiting vitamin K epoxide reductase and leads to prolonged coagulation times, measured as INR's. The active component of Coumadin® is a racemic mixture of the sodium salt chiral coumarin molecule warfarin (1).

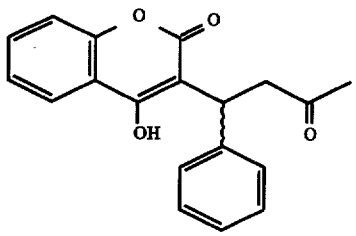

Considerable differences exist in the metabolic disposition of its two enantiomers. However, only racemic mixtures of S- and R-warfarin (1a and 1b, respectively) are clinically available. This is due to the difficulty of large scale preparation of enantiomerically pure warfarins.

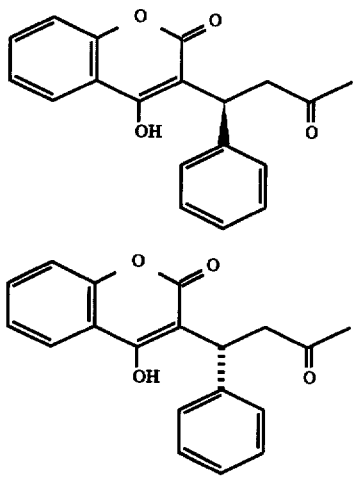

The R- and S-enantiomers of warfarin have been successfully resolved. West et al (*J. Am. Chem. Soc.* 1961, 81, 2676) used quinidine and quinine salts to obtain enantiomerically pure S- and R-warfarin, respectively. Unfortunately, their procedure had a net yield of 31% based on the amount of racemic warfarin used.

Cook et al (*J. Pharmacol. Exp. Ther.* 1979, 210(3), 391) derivatized R,S-warfarin with d-10-camphorsulfonyl chloride to give d-10-camphorsulfonates of R,S-warfarin which were separated by column chromatography. The purified R- and S-warfarin camphorsulfonates were converted to R- and S-warfarins upon treatment with 5% sodium hydroxide. The yields of R- and S-warfarin were 10.5% and 12.2%, respectively.

A variety of small scale enrichment or separation methods for racemic warfarin have been reported. Armstrong et al (*Anal. Chem.* 1994, 66, 4278) reported enantiomeric enrichment of racemic warfarin via adsorptive bubble separation. Using two different derivatized cyclodextrin collectors, enantiomeric excesses of 12% and 20% were obtained. Soini et al (*Anal. Chem.* 1994, 66, 3477) illustrate separation of racemic warfarin with capillary electrophoresis. Maltodextrin oligosaccharides were shown to separate R- and S-warfarin via an electropherogram. Bargmann-Leyder et al (*Chromatographia* 1993, 37, 433–443) describe chromatographic resolution of warfarin enantiomers using column liquid chromatography and supercritical fluid chromatography. Chiral stationary phases derived from tyrosine enabled enantiomer resolution. The enantiomeric excesses obtained were not reported. The above-noted procedures would appear to be able to resolve R- and S-warfarin; but, unfortunately, they are either not suitable for industrial scale up or provide insufficient resolution.

Dehydrowarfarin (3, $R_1$=phenyl, $R_2$=H, $R_3$=Me, and $R_{4-5}$=H, shown below) has been identified as a minor metabolite of warfarin and was first isolated and prepared by Kaminsky et al (*J. Med. Chem.* 1978, 21 (10), 1054). The procedure reported by Kaminsky et al involving copper (I) catalyzed oxidation of warfarin racemate in pyridine was shown by the present inventors to be unreliable and gave at best poor yields (<33%) of dehydrowarfarin.

Highly enantioselective hydrogenations of $\alpha,\beta$-unsaturated ketones have rarely been achieved. Recently, Ohta et al (*J. Org. Chem.* 1995, 60, 357–363) reported enantioselective hydrogenation of a series of cyclic $\alpha\beta$-unsaturated ketones using chiral phosphine catalysts. Their hydrogenation procedure failed or provided a very low enantiomeric excess when a phenyl (like that in warfarin) or phenethyl group was present on the olefin. More important to the present invention, if an acyclic $\alpha,\beta$-unsaturated ketone was used, e.g., dehydrowarfarin, the procedure of Ohta et al failed completely.

Thus, the present art is unable to industrially produce enantiomerically pure R- and S-warfarin and its analogs. Therefore, it is desirable to find an industrially useful procedure for the asymmetric synthesis of R and S warfarin and its analogs.

SUMMARY OF THE INVENTION

Accordingly, an object of the present invention is to provide a novel process for making R- or S-warfarin or analogs thereof or pharmaceutically suitable salts thereof.

This and other objects, which will become apparent during the following detailed description, have been achieved by the inventors' discovery that compounds of formula 2a or 2b or pharmaceutically acceptable salts thereof,

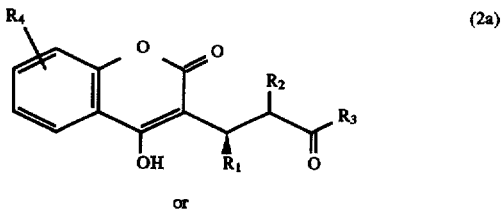

or

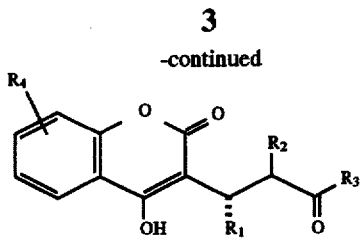

(2b)

wherein $R_1$ is selected from the group consisting of phenyl and phenyl substituted with at least one group selected from $NO_2$ and halogen;

$R_2$ is H;

$R_3$ is selected from the group consisting of $C_{1-4}$ alkyl, phenyl, and benzyl; and, $R_4$ is selected from the group consisting of H and halogen;

are formed by an asymmetric process, comprising the steps of:

a) oxidizing a racemate of formula 2 or a salt thereof to form a dehydro-compound of formula 3,

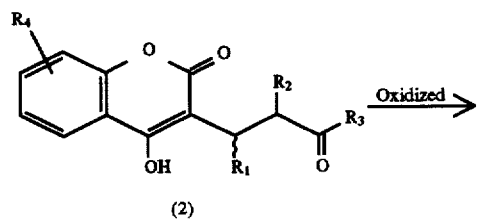

(2)

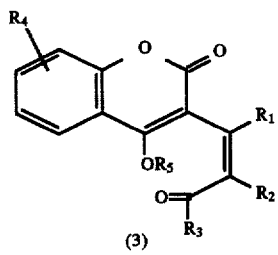

(3)

wherein $R_5$ is selected from the group consisting of H, $CH_3$, benzyl, $C_{2-8}$ acyl, Na, Li and K; and, b) asymmetrically hydrogenating a compound of formula 3 in the presence of a chiral phosphine catalyst to form a compound of formula 2a or 2b.

DETAILED DESCRIPTION OF THE INVENTION

Thus, in a first embodiment, the present invention provides a novel process for the synthesis, from the corresponding racemate, of a compound of formula 2a or 2b or pharmaceutically acceptable salt thereof,

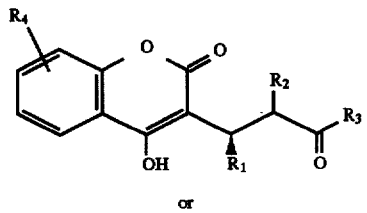

(2a)

or

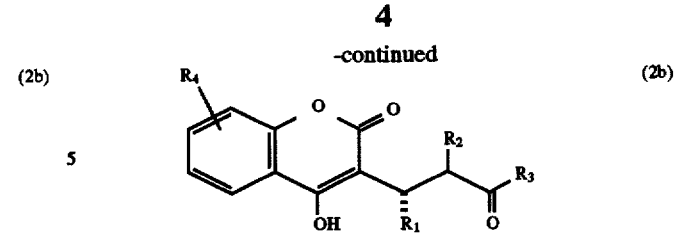

(2b)

wherein $R_1$ is selected from the group consisting of phenyl and phenyl substituted with at least one group selected from $NO_2$ and halogen;

$R_2$ is H;

$R_3$ is selected from the group consisting of $C_{1-4}$ alkyl, phenyl, and benzyl; and, $R_4$ is selected from the group consisting of H and halogen; comprising the steps of:

a) oxidizing a racemate of formula 2 to form a compound of formula 3,

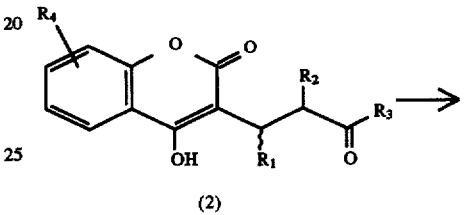

(2)

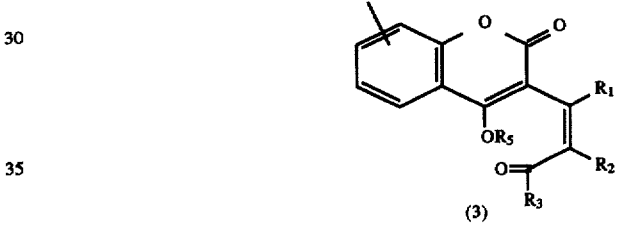

(3)

wherein $R_5$ is selected from the group consisting of H, $CH_3$, benzyl, $C_{2-8}$ acyl, Na, Li and K; and, b) asymmetrically hydrogenating a compound of formula 3 in the presence of a chiral phosphine catalyst to form a compound of formula 2a or 2b.

In a preferred embodiment, step a) is performed in the presence of CuCl, $O_2$ and pyridine.

In another preferred embodiment, in step b) $R_5$ is selected from the group consisting of $CH_3$, benzyl, $C_{1-8}$ acyl, Na, Li .and K.

In a more preferred embodiment, in step b) $R_5$ is selected from the group consisting of Me, Na, Li and K.

In a most preferred embodiment, in step b) $R_5$ is Na.

In a another preferred embodiment, a chiral phospholane-Rh(I) complex is used as the chiral phosphine catalyst in step b).

In a more preferred embodiment, in step b) the chiral phospholane is selected from the group consisting of [R,R]-Me-DuPHOS®, [S,S]-Me-DuPHOS®, [R,R]-Et-DuPHOS® and [S,S]-Et-DuPHOS®.

In a most preferred embodiment, the chiral phosphine catalyst in step b) is CODRh[S,S]Et-DuPHOS®OTf.

In a another most preferred embodiment, the chiral phosphine catalyst in step b) is CODRh[R,R]Et-DuPHOS®OTf.

In a another most preferred embodiment, the chiral phosphine catalyst in step b) is CODRh[S,S]Me-DuPHOS®OTf.

In a another most preferred embodiment, the chiral phosphine catalyst in step b) is CODRh [R,R]Me-DuPHOS®OTf.

In another preferred embodiment, in step b) a solvent selected from the group consisting of THF, isopropanol, methanol and a mixture thereof is used.

In a more preferred embodiment, methanol is used as solvent in step b).

In a another more preferred embodiment, isopropanol is used as solvent in step b).

In a another more preferred embodiment, a mixture of methanol and isopropanol is used as solvent in step b).

In another preferred embodiment, $R_1$=phenyl $R_2$=H, $R_3$=Me, and $R_{4-5}$=H.

In another preferred embodiment, $R_1$=phenyl, $R_2$=H, $R_3$=Me, $R_4$=H, and $R_5$=Na.

In another preferred embodiment, $R_1$=phenyl, $R_2$=H, $R_3$=Me, $R_4$=7-F, and $R_5$=H.

In another preferred embodiment, $R_1$=4'-nitrophenyl, $R_2$=H, $R_3$=Me, and $R_{4-5}$=H.

In another preferred embodiment, $R_1$=4'-chlorophenyl, $R_2$=H, $R_3$=Me, and $R_{4-5}$=H.

As used herein, the trademarked chiral phospholanes and phosphines are intended to correspond to the chemical species as follows,

[R,R]-Me-DuPHOS®: (−)-1,2-Bis((2R,5R)-2,5-dimethylphospholano)benzene;

[S,S]-Me-DuPHOS®: (+)-1,2-Bis((2S,5S)-2,5-dimethylphospholano)benzene;

[R,R]-Et-DuPHOS®: (−)-1,2-Bis((2R,5R)-2,5-diethylphospholano)benzene;

[S,S]-Et-DuPHOS®: (+)-1,2-Bis((2S,5S)-2,5-diethylphospholano)benzene;

CODRh[S,S]Me-DuPHOS®OTf: [(COD)Rh(1,2-Bis((2S,5S)-2,5-dimethylphospholano)benzene)]$^{+CF_3SO_3^-}$;

CODRh[R,R]Me-DuPHOS®OTf: [(COD)Rh(1,2-Bis((2R,5R)-2,5-dimethylphospholano)benzene)]$^{+CF_3SO_3^-}$;

CODRh[S,S]Et-DuPHOS®OTf: [(COD)Rh(1,2-Bis((2S,5S)-2,5-diethylphospholano)benzene)]$^{+CF_3SO_3^-}$; and CODRh[R,R]Et-DuPHOS®OTf: [(COD)Rh(1,2-Bis((2R, 5R)-2,5-diethylphospholano)benzene)]$^{+CF_3SO_3^-}$.

As used herein, "alkyl" is intended to include both branched and straight-chain saturated aliphatic hydrocarbon groups having the specified number of carbon atoms. For example, $C_{1-4}$ intended to include, methyl, ethyl, n-propyl, i-propyl, n-butyl, i-butyl, sec-butyl and t-butyl. "Fluoroalkyl" is intended to include both branched and straight-chain saturated aliphatic hydrocarbon groups having the specified number of carbon atoms, substituted with 1 or more fluorines. "Perfluoroalkyl" is intended to include both branched and straight-chain saturated aliphatic hydrocarbon groups having the specified number of carbon atoms, fully substituted with fluorines, i.e., $C_nF_{2n}$. "Halo" or "halogen" as used herein refers to fluoro, chloro, bromo, and iodo. As used herein, "acyl" is intended to include both branched and straight-chain saturated aliphatic hydrocarbon groups with a carbonyl (C=O) group at the point of attachment and having the specified number of carbon atoms. For example, $C_{2-8}$ is intended to include, acetyl, propanoyl, n-butanoyl, i-butanoyl, sec-butanoyl, etc. . . . groups.

When any variable (e.g., halogen) may occur more than one time in any constituent or formula for a compound, its definition on each occurrence is independent of its definition at every other occurrence. Thus, for example, if a group is shown to be substituted with at least one halogen, then said group may optionally be substituted with from one to however many possible halogens and halogen at each occurrence is selected independently from the defined list of possible halogens.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesutfonic, ethane disulfonic, oxalic, isethionic, and the like.

The pharmaceutically acceptable salts made by the present invention can be synthesized from the parent compound by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Suitable protic solvents may include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3- pentanol, neo-pentyl alcohol, t-pentyl alcohol, diethylene glycol monomethyl ether, diethylene glycol monoethyl ether, cyclohexanol, anisole, benzyl alcohol, phenol, or glycerol.

Suitable aprotic solvents may include, by way of example and without limitation, tetrahydrofuran (THF), dimethylformamide (DMF), dimethylacetamide (DMAC), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

SYNTHESIS

By way of example and without limitation, the present invention may be further understood by the following scheme. This scheme details the general synthetic method for preparation of compounds of formula 2a or 2b from compounds of formula 2.

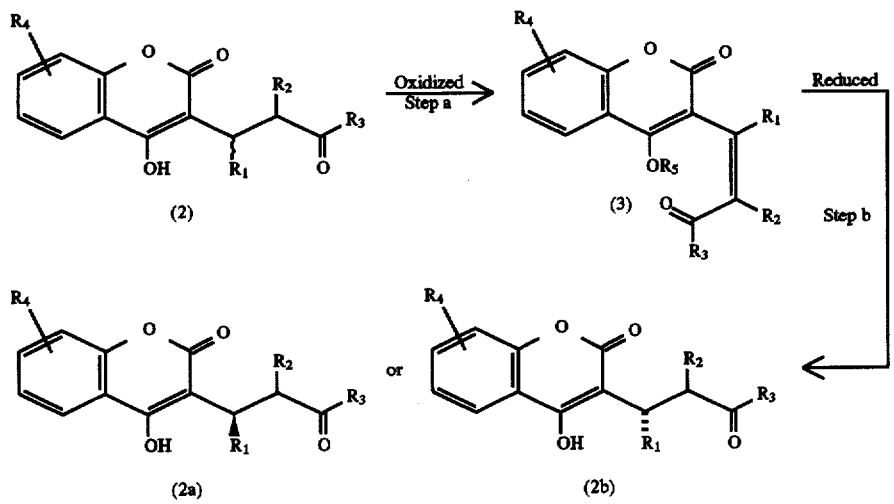

(2)   (3)   (2a) or (2b)

Step a:

Starting compounds 2 are commercially available (e.g., warfarin may be purchased from Aldrich) or may be synthesized by any method known to those of skill in the art.

Prolonged exposure of (3), specifically dehydrowarfarin, to the oxidative reaction conditions used to oxidize (2), resulted in formation of a spiro[benzofuran-2(3H),1'-cyclopentane] ring system. Formation of this by-product can be advantageously minimized by monitoring of reaction progress by, for example, thin layer chromatography.

As a preferable source of oxygen, a continuous stream of air through the reaction mixture is used. Oxygen, in place of air, could be forced through the reaction mixture. An elevated temperature of from about 30°–80° C. can be used, preferably, from about 50°–60° C. Typically, at least stoichiometric amounts (i.e., about 1 equivalent of CuCl based on the amount of compound 2) of cuprous chloride are used, preferably, from about 1–5 equivalents, more preferably, from about 1.1–1.5 equivalents. Oxidation progress can be monitored by thin layer chromatography or other methods known to those of skill in the art. The oxidation can be performed, preferably, for from 1–24 hours, more preferably, from 2–6 hours, most preferably about 3 hours. The oxidation time is dependent upon reaction scale. One of ordinary skill in the art would recognize the need to increase oxidation time, if necessary, as the reaction scale increased.

Even though the copper (I) oxidation procedure of Kaminsky et al gave at best poor yields (<33%), step a) of the present invention using copper (I) and oxygen gives oxidized product (3) in excellent yield (=98%) and purification of the crude product is not required. Thus, not only is the yield of step a) enhanced compared to that of Kaminsky et al, but the purification steps required when using the procedure of Kaminsky et al have been eliminated.

X-ray crystal structure analysis of dehydrowarfarin revealed the formation of the ring closed hemiacetal form of (3) in the presence of methanol; this tautomer arises from cis orientation of the olefinic bond. Hydrogen bonding between hydroxyl and carbonyl substituents was also observed in the crystal lattice.

Step b:

One of ordinary skill in the art would not expect to be able to hydrogenate acyclic α,β-unsaturated ketones of formula (3) using chiral phosphine catalysts with high enantioselectivity due to the ineffectiveness of the procedure of Ohta et al on acyclic α,β-unsaturated ketones. Further evidence of the inability of chiral phosphine catalysts to hydrogenate α,β-unsaturated ketones was provided by the present inventors' discovery that compounds like the following:

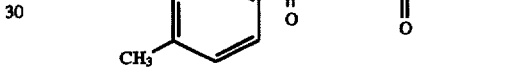

are not hydrogenated by chiral phosphine catalysts, such as CODRh[R,R]Et-DuPHOS®OTf. However, as the following description will show, the present inventors have been able to successfully hydrogenate acyclic α,β-unsaturated ketones of formula 3, which may contain a phenyl group attached to the olefin moiety, using chiral phosphine catalysts.

Asymmetric hydrogenation is performed under such conditions as to provide an enantiomeric excess (ee) of at least 50%, preferably, at least 70%, more preferably, at least 80%. Any chiral phosphine catalyst capable of providing asymmetric hydrogenation can be used. The metal used with the chiral ligand may be selected from the group consisting of transition metals, lanthanides and actinides, preferably, Ru or Rh, more preferably, Rh.

Exposure of dehydrowarfarin to methanol, a protic solvent, can cause spontaneous cyclization to a hemiketal which resists hydrogenation. Use of an aprotic solvent, such as THF, eliminates this cyclization. However, it is advantageous to protect the 4-hydroxyl group as either a salt or an ether (i.e., $R_5$ is other than H) and use a protic reaction solvent in order to limit hydrogenation times and enhance enantioselectivity. This additional step is performed after production of the dehydro-compound of formula 3 wherein $R_5$=H. Protection as the sodium salt is preferable as this eliminates two extra reaction steps inherent in the generation and deprotection of 4-methoxy-, benzyl- or acyl-derivatives. Sodium salts of coumarins (3), such as dehydrowarfarin, are readily prepared by treatment with aqueous sodium hydroxide solution. Lithium and potassium salts can likewise be formed by reaction with their respective hydroxides. Methylation of the 4-hydroxyl group can be performed using known methylation procedures. For example, methyl iodide and base or trimethylsilyl-diazomethan in $CH_2Cl_2$ can be used. Standard demethylation techniques, such as acid or BBr$_3$/Et$_2$O, can be used to recover the alcohol. Standard benzylation and acylation techniques can be used to protect the hydroxyl group with a benzyl or acyl group, respectively. When R$_5$ is CH$_3$, benzyl, C$_{2-8}$ acyl, Na, K, or Li, i.e., a protected alcohol, the closed hemiacetal form of (3) is absent.

U.S. Pat. No. 5,171,892, the contents of which are incorporated herein by reference in their entirety, describes a number of phosphine ligands which can be used in asymmetric hydrogenation catalysts. The stereochemistry of the 2- and 5-position carbons on the 5-membered phosphalono rings described in U.S. Pat. No. 5,171,892 are either R or S. The selection of the stereochemistry depends on the stereochemistry of the desired compound. For example, if an R-enantiomer is desired, one might use CODRh[S,S]Et-DuPHOS®OTf. If, however, an S-enantiomer is desired, one might use CODRh[R,R]Et-DuPHOS®OTf.

The chiral phosphine ligand used can be selected from any which when bound to a metal form a catalyst which will enable asymmetric hydrogenation. Examples of which include, but are not limited to the following:

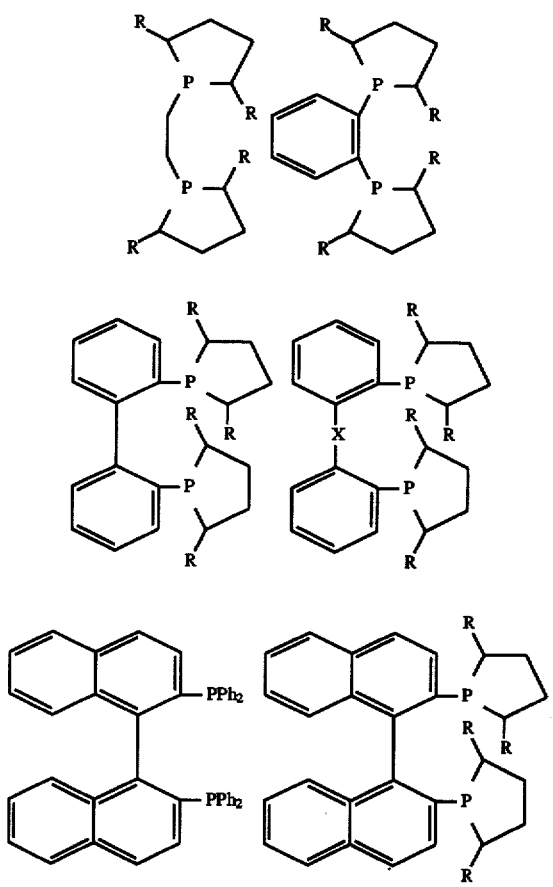

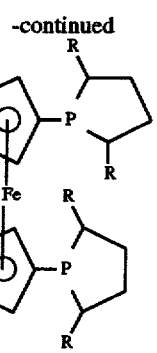

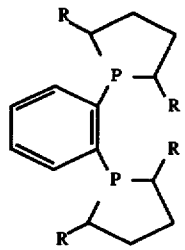

wherein X is selected from the group consisting of O, S, and NR, and R is selected from the group consisting of C$_{2-8}$ alkyl, C$_{1-8}$ fluoro- or perfluoroalkyl, phenyl, and phenyl substituted with from 1–4 substituents selected from the group consisting of halogen, C$_{1-6}$ alkyl, and NO$_2$. Other chiral phosphine ligands which can be used with the present invention are given in I. Ojima, CATALYTIC ASYMMETRIC SYNTHESIS (1993), the contents of which are incorporated herein by reference.

Hydrogenation is, preferably, performed using the homochiral 1,2-bis(phospholano)-benzene ligand (DuPHOS®; R=Me, Et) shown below;

wherein when R=Me, the ligand corresponds to Me-DuPHOS® and when R=Et, the ligand corresponds to Et-DuPHOS®. These ligands may be prepared as described in U.S. Pat. No. 5,171,892.

The chiral phosphine catalysts are prepared by reacting a phosphine ligand with a metal precursor. Typical precursor transition metal complexes suitable for use herein include, but are not limited to, [(COD)$_2$Rh]$^+$Z$^-$, wherein COD is 1,5-cyclooctadiene, and Z is BF$_4^-$, SbF$_6^-$, PF$_6^-$, CF$_3$SO$_3^-$ (OTf$^-$) or [CODRu(2-methylallyl)$_2$], preferably, [(COD)$_2$Rh]$^+$ OTf$^-$) or [CODRu(2-methylallyl)$_2$]. Catalyst preparation is usually conducted in an organic solvent (e.g., hexane, THF, or methanol) under an inert atmosphere (e.g., argon or nitrogen). The temperature is typically from 0° C. to the boiling point of the solvent used, preferably, the boiling point of the solvent. The chiral phosphine catalysts described herein can be abbreviated by omitting the counter ion Z$^-$ and the secondary ligand (e.g., COD). If no counter ion or secondary ligand is recited, then it is to be understood that the counter ion is OTf$^-$ and the secondary ligand is COD.

GENERAL PROCEDURE FOR ASYMMETRIC HYDROGENATIONS

In a dry box, a Fisher-Porter tube or bottle is charged with a coumarin (3, R$_5$≠H), deoxygenated solvent, and catalyst (0.1–0.005 mol %). After four vacuum/H$_2$ cycles, the tube is pressurized to an initial pressure of about 60 psig H$_2$. Hydrogenation is allowed to continue at about 20°–25° C. overnight (15–18 h) or until complete. Complete conversion (100%) to product is confirmed by TLC and $^1$H NMR analysis. All reactions are quantitative or nearly quantitative and are concentrated by rotary evaporation. Sodium salt derivatives are diluted with water, acidified (pH=3, glacial acetic acid) and extracted into ethyl acetate before further analysis. Reaction aliquots are removed and chromatographed on glass-backed silica preparative slides (ethyl acetate/petroleum ether, 1:1). Without further purification reaction products are analyzed for enantiomeric excess on a Chiracel OJ column (4-hydroxy derivatives, 0.1% AcOH/EtOH; 4-methoxy derivatives, 50% Hexane/EtOH).

Under otherwise standard hydrogenation conditions, [S,S] Et-DuPHOS®-Rh catalyzed hydrogenation of 3 (R$_1$= phenyl, R$_2$=H, R$_3$=Me and R$_5$=Na) in methanol was conducted at −78° C., −10° C. and 25° C. No significant change in enantioselectivity at −10° C. was observed. Qualitatively, however, the reaction rate decreased significantly on lowering of the reaction temperature; at −10° C. hydrogenation was incomplete (75% conversion to (1b)) and at −78° C. no reduction occurred. This probably reflects the lowering of the inherent reaction rate since solubility, even at −78° C., was excellent. (See Table 1)

Hydrogenation in aprotic solvents such as THF resulted in good enantiomeric excess. Protic solvents such as alcohols, methanol and isopropanol, however, gave higher enantioselectivities. Methanol is the preferable solvent. When methanol and isopropanol are used as a mixture, it is preferable to use a ratio of from 80:20 to 20:80 methanol:isopropanol, more preferably, from 70:30 to 30:70, most preferably, about 40:60. (See Tables 1 and 2.)

Results of hydrogenating coumarins (3) under various conditions are given in Tables 1 and 2. Unless otherwise noted, hydrogenations were performed at ambient temperature in methanol and the catalyst used is CODRh[A,A] DuPHOS®OTf, wherein [A,A] is either [R,R] or [S,S] and is defined in the table.

TABLE 1

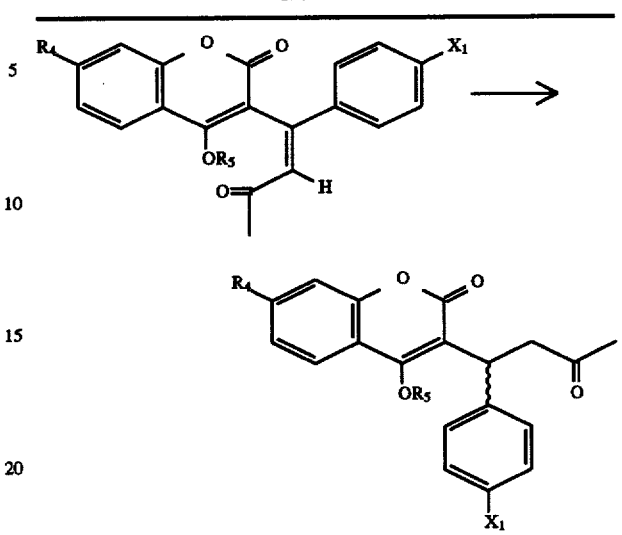

| DuPHOS Catalyst | R$_5$ | X$_1$ | R$_4$ | % ee (Enantiomer) | Comment |
|---|---|---|---|---|---|
| [R,R]Me | H | H | H | 70(S) | THF |
| [R,R]Et | Na | H | H | 81(S) | |
| [S,S]Et | Na | H | H | 86(R) | |
| [S,S]Et | Na | H | H | 88(R) | iPrOH/MeOH (60:40) |
| [R,R]Et | K | H | H | 82(S) | |
| [R,R]Et | Li | H | H | 82(S) | |
| [S,S]Et | Na | H | H | 84(R) | −10° C. 25% Reduction |
| [S,S]Et | Na | H | H | — | −78° C. 0% Reduction |
| [R,R]Et | Na | H | H | 85(S) | α-methyl benzylamine added[1] |
| [R,R]Me | Me | H | H | 86(S) | |
| [S,S]Et | Me | H | H | 89(R) | |
| [S,S]Et | Na | NO$_2$ | H | 64(R) | Reaction time = 72h |
| [R,R]Et | Na | Cl | H | 78(S) | |
| [R,R]Et | Na | H | F | 85(S) | |
| [R,R]Et | Me | H | F | 90(S) | |

[1] An equivalent, based on the amount of dehydrocoumarin, of α-methyl benzylamine was added.

TABLE 2

| DuPHOS ® Catalyst | X₃ | % ee (Enantiomer) |
|---|---|---|
| [S,S]Et | H | 78(R) |
| [S,S]Et | NO₂ | 77(R) |

Other features of the invention will become apparent in the course of the following descriptions of exemplary embodiments which are given for illustration of the invention and are not intended to be limiting thereof.

EXAMPLES

Example 1

Synthesis of Dehydrowarfarin (3, R₁=phenyl, R₂=H, R₃=Me, and R₄₋₅=H)

Copper (I) chloride (5.12g) was added to a stirred solution of racemic 3-(α-acetonylbenzyl)-4-hydroxycoumarin (10.10 g) (warfarin) in anhydrous pyridine (60 ml). The mixture was heated at 55°–60° C. while being aerated with a steady flow of air. After 6 h, thin layer chromatography ((Ethyl acetate (EA): petroleum ether (PE), 1:1), Rf (warfarin)=0.3, Rf (1)=0.1, Rf (2)=0.5) showed dehydrowarfarin and no starting material. The reaction was then cooled, diluted with water (300 mL) and acidified (2M HCl, pH=1). The mixture was extracted into ethyl acetate (5×100 mL) and the combined organic extract was then extracted with aqueous sodium hydroxide solution (8×60 mL). Reacification (2M HCl, pH=1) of the combined basic extracts gave spiro [benzofuran-3-one-2,1'-2'-phenylcyclopent-2'-en-4'-one] (dehydrowarfarin) (9.76 g, 97%) as a pale yellow solid, mp 111°–113° C. $^1$H NMR (CDCl₃) δ 2.91, d, $J_{AB}$ 18.0 Hz, H5'; 2.94, d, $J_{AB}$ 18.3 Hz, H5'; 6.73, s, H3'; 7.20, t, J 8.2 Hz, 2ArH; 7.24–7.30, m, 4ArH; 7.30–7.40, m, ArH; 7.68–7.80, m, 2ArH. $^{13}$C NMR (CDCl₃) δ 200.9, CO; 199.0, CO; 171.6, quat C; 168.0, quatC; 138.9, CH; 133.4, CH; 131.2, quat C; 131.0, CH; 128.9, CH×2; 127.3, CH×2; 125.1, CH; 122.9, CH; 120.2, quat C; 113.7, CH; 92.6, quat C; 46.1 CH₂.

Example 2

Synthesis of dehydrowarfarin, sodium salt

A Solution of sodium hydroxide (11.8 mg) in water (5 ml) was added to dehydrowarfarin (100 mg). The resultant yellow solution was stirred at room temperature for 18 h before being extracted with ethyl acetate (3×1 ml). The aqueous phase was then rotary evaporated to dryness to give a yellow oil (142 mg) which solidified on treatment with butyl chloride. $^1$H NMR (CD₃OD) δ 2.33, s, CH₃; 6.71, s, C═CH; 7.20–7.45, m, 5ArH; 7.40–7.70, m, 3ArH; 8.06, d, J7.7 Hz, ArH. $^{13}$C NMR (CD₃OD) δ 202.9, CO; 175.8, CO; 166.8, quat C; 155.2, quat C; 151.8, quat C; 143.0, quat C; 132.2, CH; 130.6, CH; 129.6, CH; 129.1, CH×2; 128.5, CH×2; 126.1, CH; 124.1, CH; 123.6, quat C; 117.2, CH; 101.2, quat C; 29.0, CH₃.

Example 3

Hydrogenation of Dehydrowarfarin-sodium salt (3; R₁=phenyl, R₂=H, R₃=Me, R₄=H, and R₅=Na)

Under a nitrogen atmosphere in a dry-box, a 100 mL Fisher-Porter tube was charged with a solution of dehydrowarfarin sodium salt (233 mg) in degassed methanol (7 mL). CODRh[S,S]Et-DuPHOS®OTf (4–5 mg) was then added to the solution and the vessel was pressurized to an initial pressure of 60 psi H₂. The reaction was allowed to stir at room temperature for 15 h. Complete conversion (100%) to product was indicated by TLC analysis. The reaction mixture was then concentrated by rotary evaporation, diluted with water (50 mL) and acidified with 2M aqueous hydrochloric acid. The aqueous solution was extracted with ethylacetate (4×25 mL) and the combined organic extract washed with brine (1×25 mL) and water (1×25 mL). Rotary evaporation of the dried extract (MgSO₄) gave R-warfarin as a pale yellow oil (221 mg) which solidified on standing (210 mg,96%). Enantiomeric excess (82% ee) of the reaction product was determined by HPLC analysis (Daicel Chiralcel OJ, 0.1% AcOH/99.9% ethanol: (R) t₁=11.58 min,(S) t₂=20.31 min). Recrystallization from water/acetone gave R-[3-(α-acetonylbenzyl)-4-hydroxycoumarin (R-warfarin) as crystalline needles, mp 170°–171° C. The enantiomeric purity of the product was determined to be >98% ee by HPLC analysis.

Example 4

Hydrogenation of Dehydrowarfarin-sodium salt (3; R₁=phenyl, R₂=H, R₃=Me, R₄=H, and R₅=Na)

Dehydrowarfarin-sodium salt was hydrogenated under the above-noted standard conditions using [R,R]-Et DuPHOS® as catalyst. S-Warfarin, 83% ee was obtained. Recrystallization from acetone/water increased enantiomeric excess to 98.9%.

Example 5

Hydrogenation of Dehydrowarfarin-sodium salt (3; R₁=phenyl, R₂=H, R₃=Me, R₄=H, and R₅=Na)

Dehydrowarfarin-sodium salt was hydrogenated under the above-noted standard conditions using [S,S]-Et DuPHOS® as catalyst. R-Warfarin, 82% ee was obtained. Recrystallization from acetone/water increased enantiomeric excess to >98%.

Example 6

Synthesis of 7-Fluorodehydrowarfarin (3; R₁=phenyl, R₂=H, R₃=Me, and R₅=Na, and R₄=F (7-position))

Copper (I) chloride (600 mg) was added to a stirred solution of 3-(α-acetonylbenzyl)-7-fluoro-4- hydroxycoumarin (1.60 g) (7-fluorowarfarin) in anhydrous pyridine (60 ml). A continuous flow of air was then passed though the solution and the reaction mixture was stirred and heated at 50°–60° C. Reaction progress was monitored by thin layer chromatography ((Ethyl acetate (EA): petroleum ether (PE), 1:1), Rf (7-fluorowarfarin) =0.25, Rf (7-fluorodehydrowarfarin)=0.2). After 3 h the reaction was poured into water (100 ml), acidified (pH=1, conc. HCl) and extracted into methylene chloride (3×50 ml). The combined organic extract was then extracted into saturated sodium bicarbonate solution and the phases were separated. The aqueous phase was washed with methylene chloride (1×50 ml) and then reacidified (pH=1, conc. HCl) to give a precipitate. Filtration then afforded pure 7-fluorodehydrowarfarin (983 mg) as an off-white solid, mp 193° C. (decomp.). Found: 325.0869. $C_{19}H_{14}O_4F$ ((M+H)$^+$) requires 325.0876. $^1$H NMR (CDCl$_3$) δ 1.85, s, CH$_3$; 5.66, s, C=CH; 6.69, d, J7.0 Hz, ArH; 7.02, t, J7.7 Hz, ArH; 7.14, s, ArH; 7.20–7.45, m, 4ArH; 7.95, t, J6.2 Hz, ArH. $^{19}$F NMR (CDCl$_3$) δ 104.4.

Example 7

Synthesis of 7-Fluorodehydrowarfarin, sodium salt (3; $R_1$=phenyl, $R_2$=H, $R_3$=Me, and $R_5$=Na, and $R_4$=F)

A solution of sodium hydroxide (19 mg) in water (5 ml) was added to 7-fluorodehydrowarfarin (170 mg). The resultant yellow solution was stirred at room temperature for 18 h before being extracted with ethyl acetate (3×1 ml). The aqueous phase was then rotary evaporated to dryness to give a yellow oil (191 mg) which solidified on treatment with butyl chloride. $^1$H NMR (CD$_3$OD) δ 2.07, s with fine splitting, CH$_3$; 6.44, s with fine splitting, C=CH; 6.70–6.90, m, 2ArH; 7.00–7.10, m, 3ArH; 7.30–7.40, m, 2ArH; 7.82, m, ArH. $^{19}$F NMR (CD$_3$OD) δ 110.9. $^{13}$C NMR (CD$_3$OD) δ 202.8, CO; 175.1, CO; 166.5, quat C; 156.3, quat C with fine splitting; 151.4, quat C; 142.9, quat C; 130.5, CH; 129.6, CH; 129.1, CH×2; 128.4, CH×2; 128.3, quat C; 128.2, quat C; 120.4, CH; 111.7, CH with fine splitting; 104.0, CH with fine splitting; 100.3, quat C; 29.1, CH$_3$.

Example 8

Synthesis of dehydroacenocoumarin (3, $R_1$=4'-nitrophenyl and $R_2$=H, $R_3$=Me, $R_4$=H, and $R_5$=Na)

The procedure of Examples 1 and 5 were used to obtain the title compound from dehydroacenocoumarin. Yield= 97%. $^1$H NMR (CDCl$_3$/d$_8$THF) δ 1.44, s, CH$_3$; 6.51, s, C=CH; 7.00–6.85, m, 2ArH; 7.06, d, J8.4 Hz, 2ArH; 7.17, t, J7.7 Hz, ArH; 7.58, d, J7.7 Hz, ArH; 7.76, d, J8.1 Hz, 2ArH.

The procedure of Example 2 was followed to obtain the sodium salt of the title compound. Sodium salt: $^1$H NMR (CD$_3$OD) δ 2.22, s, CH$_3$; 6.56, s, C=CH; 7.25–7.10, m, 2ArH; 7.47, t, J8.4 Hz, ArH; 7.66, d, J8.8 Hz, 2ArH; 7.90, d, J8.1 Hz, ArH; 8.12, d, J8.8 Hz, 2ArH.

Example 9

Synthesis of dehydrocoumachlor (3, $R_1$=4'-chlorophenyl and $R_2$=H, $R_3$=Me, $R_4$=H, and $R_5$=Na)

The procedure of Examples 1 and 5 were used to obtain the title compound from hydrocoumachlor. Yield=49%. $^1$H NMR (CDCl$_3$) δ 1.88, s, CH$_3$; 5.70, s, C=CH; 7.05–7.15, m, 2ArH; 7.20–7.30, m, 4ArH; 7.46, t, J7.3 Hz, ArH; 7.96, d, J8.1 Hz, ArH.

The procedure of Example 2 was followed to obtain the sodium salt of the title compound. Sodium salt: $^1$H NMR (CD$_3$OD) δ 2.17, s, CH$_3$; 6.53, s, C=CH; 7.05–7.15, m, 4ArH; 7.40–7.60, m, 3ArH; 7.91, d, J8.1 Hz, ArH.

UTILITY SECTION

In man, S-warfarin (1a) is 5 to 8 times more potent an anticoagulant than its antipode and is metabolized almost exclusively to 7-hydroxy- and 6-hydroxy warfarin by P450 CYP2C9. Conversely R-warfarin (1b), in addition to being reduced to warfarin alcohol, shows less regioselectivity in the various hydroxylated products produced, and its metabolism does not involve P450 CYP2C9. The conversion of S-warfarin (1a) to the biologically inactive S-7-hydroxywarfarin metabolite by the above human cytochrome accounts for 60–70% of an administered dose of S-warfarin (1a). Inhibition of this cytochrome pathway by other drugs is believed to be the primary cause of metabolic drug interactions observed with the clinical use of warfarin. Reduction or elimination of P450 CYP2C9's involvement in metabolism might therefore provide an anticoagulant with an improved pharmacological profile. This might be achieved by blocking the metabolic hydroxylation sites on the coumarin ring or by administration of enantiomerically pure R-warfarin (1b).

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A process for the synthesis of a compound of formula 2a or 2b or pharmaceutically acceptable salt thereof,

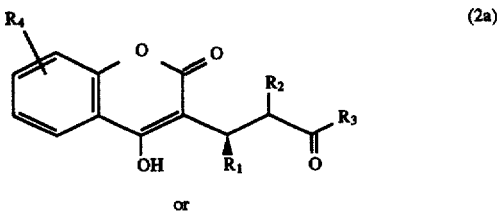

(2a)

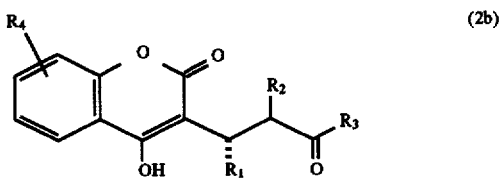

(2b)

wherein $R_1$ is selected from the group consisting of phenyl and phenyl substituted with at least one group selected from NO$_2$ and halogen;

$R_2$ is H;

$R_3$ is selected from the group consisting of $C_{1-4}$ alkyl, phenyl, and benzyl; and, $R_4$ is selected from the group consisting of H and halogen; comprising the steps of:

a) oxidizing a racemate of formula 2 to form a compound of formula 3,

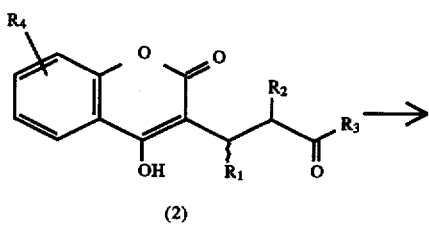

(2)

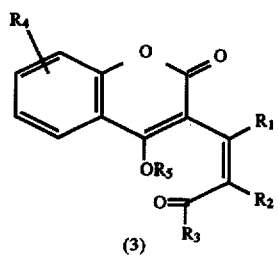

(3)

wherein $R_5$ is selected from the group consisting of H, $CH_3$, benzyl, $C_{2-8}$ acyl, Na, Li and K; and, b) asymmetrically hydrogenating a compound of formula 3 in the presence of a chiral phosphine catalyst to form a compound of formula 2a or 2b.

2. The process according to claim 1, wherein step a) is performed in the presence of CuCl, $O_2$ and pyridine.

3. The process according to claim 1, wherein in step b) $R_5$ is selected from the group consisting of $CH_3$, benzyl, $C_{1-8}$ acyl, Na, Li and K.

4. The process according to claim 3, wherein in step b) $R_5$ is selected from the group consisting of Me, Na, Li and K.

5. The process according to claim 3, wherein in step b), $R_5$ is Na.

6. The process according to claim 1, wherein a chiral phospholane-Rh(I) complex is used as the chiral phosphine catalyst in step b).

7. The process according to claim 6, wherein the chiral phospholane is selected from the group consisting of (−)-1,2-bis ((2R, 5R)-2,5-dimethylphospholano)benzene, (+)-1,2-bis((2S,5S)-2,5-dimethylphospholano)benzene, (−)-1,2-bis( (2R,5R)-2,5-diethylphospholano)benzene, and 1,2-bis((2S, 5S)-2,5-diethylphospholano)benzene.

8. The process according to claim 7, wherein the chiral phosphine catalyst in step b) is [(COD)Rh(1,2-Bis((2S,5S) -2,5-diethylphospholano)benzene)]$^+CF_3SO_3^-$.

9. The process according to claim 7, wherein the chiral phosphine catalyst in step b) is [(COD)Rh(1,2-Bis((2R,5R) -2,5-diethylphospholano)benzene)]$^{+CF}_3SO_3^-$.

10. The process according to claim 7, wherein the chiral phosphine catalyst in step b) is [(COD)Rh(1,2-Bis((2S,5S)- 2,5-dimethylphospholano)benzene)]$^+CF_3SO_3^-$.

11. The process according to claim 7, wherein the chiral phosphine catalyst in step b) is [(COD)Rh(1,2-Bis((2R,5R) -2,5-dimethylphospholano)benzene)]$^+CF_3^-$.

12. The process according to claim 1, wherein in step b) a solvent selected from the group consisting of THF isopropanol, methanol and a mixture thereof is used.

13. The process according to claim 12, wherein methanol is used as solvent in step b).

14. The process according to claim 12, wherein isopropanol is used as solvent in step b).

15. The process according to claim 12, wherein a mixture of methanol and isopropanol is used as solvent in step b).

16. The process according to claim 1, wherein $R_1$=phenyl $R_2$=H, $R_3$=Me, and $R_{4-5}$=H.

17. The process according to claim 1, wherein $R_1$=phenyl, $R_2$=H, $R_3$=Me, $R_4$=H, and $R_5$=Na.

18. The process according to claim 1, wherein $R_1$=phenyl, $R_2$=H, $R_3$=Me, $R_4$=7-F, and $R_5$=H.

19. The process according to claim 1, wherein $R_1$=4'-nitrophenyl, $R_2$=H, $R_3$=Me, and $R_{4-5}$=H.

20. The process according to claim 1, wherein $R_1$=4'-chlorophenyl, $R_2$=H, $R_3$=Me, and $R_{4-5}$=H.

* * * * *